United States Patent
Flick et al.

(10) Patent No.: US 9,643,898 B2
(45) Date of Patent: May 9, 2017

(54) ALKANOL TO ALKYLENE CONVERSION USING AT LEAST TWO DIFFERENT CATALYSTS IN SEQUENTIAL ORDER

(71) Applicant: Dow Global Technologies LLC, Midland, MI (US)

(72) Inventors: Derrick W. Flick, Friendswood, TX (US); Mark W. Stewart, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/030,634

(22) PCT Filed: Nov. 17, 2014

(86) PCT No.: PCT/US2014/065904
§ 371 (c)(1),
(2) Date: Apr. 20, 2016

(87) PCT Pub. No.: WO2015/088707
PCT Pub. Date: Jun. 18, 2015

(65) Prior Publication Data
US 2016/0244383 A1    Aug. 25, 2016

Related U.S. Application Data

(60) Provisional application No. 61/915,799, filed on Dec. 13, 2013.

(51) Int. Cl.
| | | |
|---|---|---|
| *C07C 1/24* | (2006.01) | |
| *B01J 21/04* | (2006.01) | |
| *B01J 29/40* | (2006.01) | |

(52) U.S. Cl.
CPC .............. *C07C 1/24* (2013.01); *B01J 21/04* (2013.01); *B01J 29/40* (2013.01); *C07C 2521/04* (2013.01); *C07C 2529/40* (2013.01); *Y02P 20/52* (2015.11)

(58) Field of Classification Search
CPC ....... C07C 1/24; C07C 11/04; C07C 2529/40; C07C 2521/04; B01J 21/04; B01J 29/40
See application file for complete search history.

(56) References Cited

U.S. PATENT DOCUMENTS

| | | | |
|---|---|---|---|
| 3,894,107 A | | 7/1975 | Butter et al. |
| 3,911,041 A | | 10/1975 | Kaeding et al. |
| 4,232,179 A | | 11/1980 | Valladares Barrocas et al. |
| 4,234,752 A | | 11/1980 | Wu et al. |
| 4,302,357 A | | 11/1981 | Kojima et al. |
| 4,396,789 A | * | 8/1983 | Barrocas .............. C07C 1/24 585/639 |
| 4,529,827 A | | 7/1985 | Drake |
| 4,542,252 A | * | 9/1985 | Graziani ............ B01J 8/0453 585/640 |
| 4,670,620 A | | 6/1987 | Jacobs et al. |
| 4,873,392 A | | 10/1989 | Le Van Mao |
| 6,489,515 B2 | | 12/2002 | Kambe et al. |
| 6,797,851 B2 | | 9/2004 | Martens et al. |
| 2008/0156692 A1 | | 7/2008 | de Rezende Pinho et al. |
| 2013/0178674 A1 | | 7/2013 | Taheri et al. |

FOREIGN PATENT DOCUMENTS

| | | |
|---|---|---|
| GB | 100994 A | 7/1916 |
| WO | 2008067627 A2 | 6/2008 |
| WO | 2008080363 A1 | 7/2008 |
| WO | 2009098262 A1 | 8/2009 |
| WO | 2010085708 A2 | 7/2010 |
| WO | 2011161045 A1 | 12/2011 |

OTHER PUBLICATIONS

PCT/US2014/065904, International Search Report and Written Opinion with a mailing date of Feb. 19, 2015.
PCT/US2014/065904, International Preliminary Report on Patentability with a mailing date of Jun. 23, 2016.

* cited by examiner

*Primary Examiner* — Sharon Pregler

(57) ABSTRACT

Effect adiabatic, catalytic alkanol (alcohol) dehydration using two or more sequential dehydration catalyst beds each of which has disposed therein a different catalyst and, preferably, eliminating heating and heating apparatus disposed between each sequential pair of dehydration catalyst beds.

9 Claims, No Drawings

ALKANOL TO ALKYLENE CONVERSION USING AT LEAST TWO DIFFERENT CATALYSTS IN SEQUENTIAL ORDER

The present application claims the benefit of U.S. Provisional Application No. 61/915,799, filed on Dec. 13, 2013.

This invention relates generally to an adiabatic process for catalytically converting an alcohol contained in an alcohol feedstream to its corresponding olefin and particularly to such a process wherein two or more sequential dehydration catalyst beds, each of which comprises a different catalyst, are used to effect such a conversion and still more particularly to doing so without reheating effluent from one dehydration catalyst bed to an elevated temperature before introducing such effluent as a feed stream to the next sequential dehydration catalyst bed. Where there are two sequential dehydration catalyst beds, one may refer to them as a first dehydration catalyst bed and a second dehydration catalyst bed.

Ethylene finds many uses in a variety of applications including industrial chemicals, consumer products, polymers, plastics and surfactants. While ethylene production predominantly stems from petroleum resources via steam cracking of petroleum-derived feed stocks such as naphtha, ethane/propane or gas condensates, skilled artisans continue to seek routes that do not employ cracking.

In a typical alcohol dehydration process, skilled artisans understand that the process is endothermic and apply heat to a reaction mixture that contains the alcohol before the reaction mixture contacts a catalyst bed. As the reaction mixture contacts an adiabatic catalyst bed, a reaction ensues during which temperature, and consequently, catalyst activity both drop off. In some adiabatic reactor setups where multiple reactors are linked in series, application of heat comes by way of injection of heat carrying fluid between the reactors (see e.g. Taheri et al. below for dehydration of ethanol to ethylene) or use of heaters interspersed between reactors United States Patent Application Publication (USPAP) 2013/0178674 (Taheri et al.) discloses a reactor that comprises a multi-stage single vessel or multiple reactor vessels wherein each stage or vessel has a different length, internal diameter and volume than the other stages or vessels, with the vessels and stages being connected in parallel or in series. Taheri et al. refers to GB 516,360 for teachings about multiple reactor vessels connected in series with a heating arrangement to supply required energy to each vessel for optimum control. Because this arrangement is adiabatic in nature, the temperature in any one stage decreases continuously as the dehydration reaction proceeds. To ensure maintenance of the overall rate of reaction, inter-stage heat exchangers heated by, e.g., superheated inert gas stream, are included between successive reactor stages to provide the necessary thermal energy to sustain the reactions from stage to stage. Each stage has an optimized operating temperature of from 300 degrees centigrade (° C.) to 550° C., preferably from 350° C. to 500° C. at the inlet to each stage and at 250° C. to 500° C., preferably from 300° C. to 450° C. at the outlet to each stage.

U.S. Pat. No. 3,894,107 (Butter et al.) teaches a process for converting, among other materials, alcohols, by contacting such materials with a particular type of aluminosilicate molecular sieve catalyst at elevated temperatures of, for example, 500° F. to 1000° F. (280° C. to 538° C.). The catalyst is a zeolite that has a silica to alumina ratio of at least 12. The zeolite is exemplified by ZSM-5, ZSM-11, ZSM-12 and ZSM-21. See also WO 2011/002699.

U.S. Pat. No. 4,232,179 (Barrocas et al.) discloses preparation of ethene in the presence of catalysts using adiabatic reactors, either in parallel or in series, at temperatures within a range of from 180° C. to 600° C. The catalyst is selected from silica, alumina, silica-alumina, refractory metal oxides, zeolites, phosphoric acid supported on carbon, calcium phosphates and calcium molybdates. See also U.S. Pat. No. 4,396,789 (Barrocas et al.) for recycling unreacted ethanol and application of heat in intermediate stages of, or between adiabatic reactors used in, such preparation with ethanol being introduced into the first of the adiabatic reactors at a temperature of from 400° C. to 520° C.

Other known alcohol (alkanol) dehydration catalysts include alumina, especially chi-alumina, in U.S. Pat. No. 4,529,827 (Drake), zeolite-type catalysts such as ZSM-5 type zeolite catalysts in U.S. Pat. No. 4,670,620 (Jacobs et al.) and U.S. Pat. No. 4,873,392 (Le Van Mao), and gamma alumina, silica-alumina zeolites such as H-ZSM-5 and silicoaluminophosphate or SAPO catalysts in European Patent Publication (EP) 2,594,546. See also U.S. Pat. No. 4,234,752 (Wu et al.) for gamma alumina, and British Patent (GB) 1,009,943 U.S. Pat. No. 3,911,041 (Kaeding et al.) for a porous solid containing a zeolitic aluminosilicate as well as WO 2009/098262 and its counterpart Australian Patent (AU) 2013200006 (Minoux et al.).

EP 2,196,444 (Vermeiren) discloses a process for making alpha olefins from biologically derived ethanol that includes, as one step, dehydrating ethanol to recover an ethylene stream which is then oligomerized. Average catalyst bed temperatures for dehydration range from 280° C. to 500° C., advantageously from 280° C. to 450° C., more advantageously from 300° C. to 400° C., and preferably from 330° C. to 380° C. The catalyst may be any acid catalyst capable of causing the dehydration of alcohol with examples including zeolites, modified zeolites, silica-alumina, alumina, and SAPOs. A specific catalyst example is a crystalline silicate with a Si/Al ratio of at least 100 such as ZSM-5.

A desire exists among skilled artisans to find ways to simplify alcohol dehydration processes and, concurrently reduce costs associated with such processes.

In some aspects, this invention is an adiabatic process for catalytically converting an alcohol contained in an alcohol feedstream to its corresponding olefin, which comprises feeding the alcohol feedstream to a first dehydration catalyst bed in a series of two or more sequential dehydration catalyst beds under a first set of dehydration conditions to yield a partially dehydrated alcohol feedstream with a first olefin content and then feeding the partially dehydrated alcohol feedstream to a second sequential dehydration catalyst bed under a second set of dehydration conditions to yield a dehydrated alcohol feedstream with a second olefin content, the second olefin content being greater than the first olefin content, the first and second catalyst beds in each pairing of first and second catalyst beds comprising different catalysts and the first and second sets of dehydration conditions differing from one another by at least temperature with the first set of dehydration conditions comprising a temperature higher than the temperature of the second set of dehydration conditions. When the series of sequential catalyst beds comprises three or more sequential catalyst beds, the designation of first and second is suitably replaced by wording such as "one" in place of "first" and "the next in sequence" in place of "second". In other words, this invention relates to any two or more sequential dehydration catalyst beds in a series of sequential dehydration catalyst beds. In some aspects of this invention, the first dehydration catalyst bed contains or comprises gamma alumina.

In some aspects of this invention, the second dehydration catalyst bed contains a crystalline aluminosilicate zeolite catalyst. The crystalline aluminosilicate zeolite catalyst may be ZSM-5.

In some aspects of this invention, the first set of dehydration conditions includes a temperature within a range of from 325° C. to 425° C.

In some aspects of this invention, the second set of dehydration conditions includes a temperature within a range of from 250° C. to less than 375° C.

In some aspects of this invention where three or more dehydration catalyst beds are aligned and used in sequential order, one suitably selects catalysts for use in each of such beds to efficiently effect alcohol dehydration therein with minimal unwanted side reactions that yield products other than a desired olefin. An illustrative arrangement of three sequential dehydration catalyst beds, nominally Bed One, Bed Two and Bed Three, comprises alumina in Bed One, SAPO-34 in Bed Two and ZSM-5 in Bed Three The use of different dehydration catalyst beds with different dehydration conditions allows one to reduce at least the number of heaters or heat carrying fluid means or both and eliminate costs associated with eliminated heaters that one would otherwise have to use to heat effluent from one reactor up to a dehydration temperature before feeding it to a second reactor. An added benefit of reducing or eliminating heat carrying fluid means is a concurrent reduction in necessary reactor and equipment volume as well as simplification of purification as there is no longer a need to remove heat carrying fluid where none is present and small amounts of heat carrying fluid, where there is a reduction in amount rather than elimination, require less reactor and equipment volume than one must use without such reduction. In the adiabatic process of this invention, one can feed the effluent from a first dehydration catalyst bed directly to a second dehydration catalyst bed without heating that effluent to the temperature needed for the first dehydration catalyst bed as the second dehydration catalyst bed operates efficiently at temperatures below those of the first dehydration catalyst bed. In some instances, such as those where the effluent from the first dehydration catalyst bed is at a temperature above that at which the second dehydration catalyst bed efficiently operates to effect dehydration of alcohol contained in such effluent, one may further cool such effluent, e.g. by use of a cooling fluid or a cooling apparatus, before introducing the effluent to the second dehydration catalyst bed. Once the effluent from the first dehydration catalyst bed passes through the second dehydration catalyst bed, one can pass the effluent, or unreacted portions thereof, to a subsequent dehydration bed with a different dehydration catalyst that can operate efficiently at temperatures below those of the second dehydration catalyst or a heater that can increase the effluent or effluent portion temperature to a temperature within the range suitable for the first dehydration catalyst bed or the second dehydration catalyst bed depending upon whether the next reactor in series contains the first dehydration catalyst bed or the second dehydration catalyst bed.

The aforementioned adiabatic process and its variations have utility in that they effectively convert an alkanol (alcohol) to its corresponding alkene (e.g. ethylene where the alcohol is ethanol) at a reduced capital cost because one does not have to effect reheating of effluent (contains partially converted alcohol as well as unreacted alcohol) from a first dehydration catalyst bed before it enters a second sequential dehydration catalyst bed as its feed stream. Where there are multiple pairings of such first and second dehydration catalyst beds connected in series, one effectively reduces heating stages by one-half, eliminating heating between the first and second dehydration catalyst beds in a pair and reserving heating stages to follow each second dehydration catalyst bed when a subsequent pair of first and second dehydration catalyst bed follows such second dehydration catalyst bed. An additional benefit is that the reactant/effluent stream has to go through fewer heating steps. See U.S. Pat. No. 6,489,515 for a discussion of issues related to decomposition of materials during heating steps that cause impurities to form due to high wall/furnace temperatures needed to heat gases for an endothermic reaction.

In some aspects of the above adiabatic process, the first dehydration catalyst bed contains gamma alumina ($\gamma$-$Al_2O_3$). In these and other aspects of the above adiabatic process, the second dehydration catalyst bed contains a crystalline aluminosilicate zeolite catalyst.

In some aspects of the above adiabatic process, the crystalline aluminosilicate zeolite catalyst is ZSM-5.

In some aspects of the above adiabatic process, the first set of dehydration conditions includes an inlet temperature for the first dehydration catalyst bed within a range of from 300° C. to 500° C., preferably from 325° C. to 450° C., and more preferably from 375° C. to 425° C. These temperatures lead to an outlet temperature within a range that is typically from 315° C. to 330° C., but can range as low as 250° C.

In some aspects of the above adiabatic process, the second set of dehydration conditions includes an inlet temperature for the second dehydration catalyst bed within a range of from 250° C. to less than 375° C., preferably from 300° C. to 350° C. These temperatures lead to an outlet temperature range that is typically from 240° C. to 270° C., but can range as low as 210° C.

In some aspects of the above adiabatic process, one can introduce a third dehydration catalyst bed (e.g. with a catalyst such as SAPO-34) intermediate between the first and second catalyst beds with an operating temperature intermediate between that of each of the first and second catalyst beds or have the third catalyst bed follow the second catalyst bed in any series of first, second and third catalyst beds provided such third sequential catalyst bed has an operating temperature that is desirably less than that of the second catalyst bed. One may also introduce one or more additional catalyst beds should one choose to do so. Another means of ensuring that the inlet temperature to the second catalyst bed is within reason involves cooling effluent from the first catalyst bed to a temperature suitable for the second catalyst bed.

EXAMPLES 1 THROUGH 8 AND CEx A THROUGH F

Use two sequential reactors, nominally, "Reactor One" and "Reactor Two", to effect a series of experiments at Reactor One inlet temperatures of 375° C., 400° C. and 425° C. with catalyst bed dimensions being 2.77 centimeters (cm) in diameter and either 28 inches (71.1 cm) in length when the catalyst bed contains only one catalyst or 32 inches (81.3 cm) in length when such catalyst bed contains two catalysts, also known as "layered catalysts" or "stacked catalysts". Evaluate catalyst bed performance in terms of ethanol conversion, ethylene selectivity and ethylene yield. Denstone™ refers to Denstone™ 57 ceramic beads commercially available from Saint-Gobain NorPro. Alumina refers to ⅛ inch (0.32 cm) smooth extrudates of $\gamma$-$Al_2O_3$ commercially available from Clariant under the trade designation CS331-5 Ether Cleavage Catalyst. ZSM-5 is a 1/16 inch (0.16 cm) extrudate of 75 wt % ZSM-5 and 25 wt % γ-$Al_2O_3$ commercially available from Clariant under the trade designation T-2559.

In all of the examples for this series of experiments, the feed to Reactor One contains ethanol and water in the feed at a fixed volumetric flow rate (6.5 ml/min of 190 proof ethanol and 0.5 ml/min of water) with 175 standard cubic centimeters per minute (sccm) nitrogen as an internal standard for gas chromatograph analysis. The ethanol feed for the study is a 95% Ethanol/5% water mixture (Pure™ 190 Proof Ethanol, USP Excipient) commercially available from Archer Daniels Midland Company. The water is deionized (DI) water.

For CEx A, load Reactor One with a mixture of 89.1 g of the CS331-5 and 277 g of Denstone to provide a bed that is 28 inches (71.12 cm) in length. Load Reactor Two with 90 grams (g) of CS331-5 mixed with 277 g of Denstone to provide a bed that is 28 inches (71.12 cm) in length. Set Reactor One inlet temperature to 375° C. and use the Reactor One outlet temperature (321° C.) as the inlet temperature for Reactor Two. Effluent from Reactor One shows an ethanol (EtOH) conversion of 68.4% for an ethylene ($C_2H_4$) selectivity of 67.4% and a $C_2H_4$ yield of 46.1%. After Reactor Two, EtOH conversion rises to 70.5% for a $C_2H_4$ selectivity of 71.1% and a $C_2H_4$ yield of 50.1%. The outlet temperature for Reactor Two is 267° C.

For CEx B, replicate CEx A, but change the Reactor One inlet and outlet temperatures to, respectively, 400° C. and 328° C. Effluent from Reactor One shows an EtOH conversion of 74.5% for a $C_2H_4$ selectivity of 77.1% and a $C_2H_4$ yield of 57.4%. After Reactor Two, the EtOH conversion rises to 76.0% for a $C_2H_4$ selectivity of 77.3% and a $C_2H_4$ yield of 58.8%. The outlet temperature for Reactor Two is 268° C.

For CEx C, replicate CEx A, but change the Reactor inlet and outlet temperatures to, respectively, 425° C. and 332° C. Effluent from Reactor One shows an EtOH conversion of 81.7% for a $C_2H_4$ selectivity of 84.8% and a $C_2H_4$ yield of 69.3%. After Reactor Two, the EtOH conversion rises to 83.2% for a $C_2H_4$ selectivity of 85.3% and a $C_2H_4$ yield of 71.0%. The outlet temperature for Reactor Two is 271° C.

For Ex 1, replicate CEx A but substitute 90.1 g of ZSM-5 extrudates (T-2559) for the 90 grams of CS331-5 in Reactor Two's dehydration catalyst bed. Effluent from Reactor One shows an EtOH conversion of 68.8% for a $C_2H_4$ selectivity of 68.2% and a $C_2H_4$ yield of 46.9%. After Reactor Two, the EtOH conversion rises to 80.5% for a $C_2H_4$ selectivity of 87.5% and a $C_2H_4$ yield of 70.4%. The outlet temperatures for Reactors One and Two are, respectively, 323° C. and 219° C.

For Ex 2, replicate Ex 1 but change the Reactor One inlet temperature to 400° C. Effluent from Reactor One shows an EtOH conversion of 75.0% for a $C_2H_4$ selectivity of 77.4% and a $C_2H_4$ yield of 58.0%. After Reactor Two, the EtOH conversion rises to 83.1% for a $C_2H_4$ selectivity of 90.6% and a $C_2H_4$ yield of 75.3%. The outlet temperatures for Reactors One and Two are, respectively, 325° C. and 241° C.

For Ex 3, replicate Ex 2 but change the Reactor inlet temperature to 425° C. Effluent from Reactor shows an EtOH conversion of 82.2% for a $C_2H_4$ selectivity of 85.1% and a $C_2H_4$ yield of 70.0%. After Reactor Two, the EtOH conversion rises to 89.7% for a $C_2H_4$ selectivity of 96.4% and a $C_2H_4$ yield of 86.5%. The outlet temperatures for Reactors One and Two are, respectively, 330° C. and 252° C.

A comparison of the data for CEx A through CEx C with that of Ex 1 through Ex 3 shows that use of ZSM-5 rather than γ-$Al_2O_3$ in Reactor Two shows improvement in EtOH conversion, ethylene ($C_2H_4$) selectivity and $C_2H_4$ yield. Ex 1 through Ex 3 show the effectiveness of the using two different dehydration catalyst beds with the absence of reheating effluent between the two catalyst beds. The use of the second dehydration catalyst bed in Reactor Two with no reheating of the feed stream after the catalyst bed in Reactor One leads to higher EtOH conversion and $C_2H_4$ selectivity than possible with two sequential beds of a single dehydration catalyst.

For Ex 4, replicate Ex 1, but change the Reactor One catalyst bed such that it contains a first catalyst portion of 90.0 g of $Al_2O_3$ extrudate (CS331-5) mixed with 165 g of Denstone in front of a second catalyst portion of 60.0 g of ZSM-5 extrudates (T-2559) mixed with 105 g of Denstone to provide a total bed length of 32 inches (81.3 cm). Effluent from Reactor One shows an EtOH conversion of 85.1% for a $C_2H_4$ selectivity of 87.0% and a $C_2H_4$ yield of 74.0%. After the Reactor Two, the EtOH conversion changes to 84.6% for a $C_2H_4$ selectivity of 93.1% and a $C_2H_4$ yield of 78.8%. The outlet temperatures for first Reactors One and Two are, respectively, 258° C. and 248° C. The ten degree difference in outlet temperature suggests that $Al_2O_3$ in the Reactor Two catalyst bed has relatively low catalytic activity, especially with respect to the layered catalyst in the catalyst bed of Reactor One.

For Ex 5, replicate Ex 4 but change the Reactor One inlet temperature to 400° C. Effluent from Reactor One shows an EtOH conversion of 92.6% for a $C_2H_4$ selectivity of 96.2% and a $C_2H_4$ yield of 89.1%. After Reactor Two, the EtOH conversion changes to 92.6% for a $C_2H_4$ selectivity of 97.9% and a $C_2H_4$ yield of 90.7%. The outlet temperatures for Reactors One and Two are, respectively, 265° C. and 256° C.

Ex 4 and 5 show that one can use a layered catalyst combination of two catalysts in the bed of Reactor One with very satisfactory improved results relative to Ex 1-3 and CEx A-CB-D.

For CEx D, replicate CEx B, but heat the Reactor One effluent to provide a Reactor Two inlet temperature of 375° C. Effluent from Reactor One shows an EtOH conversion of 68.9% for a $C_2H_4$ selectivity of 68.6% and a $C_2H_4$ yield of 47.3%. After Reactor Two, the EtOH conversion rises to 75.9% for a $C_2H_4$ selectivity of 86.0% and a $C_2H_4$ yield of 65.3%.

For CEx E, replicate CEx C, but change the inlet temperatures for Reactors One and Two to 400° C. Effluent from Reactor One shows an EtOH conversion of 74.8% for a $C_2H_4$ selectivity of 77.5% and a $C_2H_4$ yield of 58.0%. After Reactor Two, the EtOH conversion rises to 85.0% for a $C_2H_4$ selectivity of 93.8% and a $C_2H_4$ yield of 79.8%.

For CEx F, replicate CEx E, but change the inlet temperatures for Reactors One and Two to 425° C. Effluent from Reactor One shows an EtOH conversion of 81.8% for a $C_2H_4$ selectivity of 84.9% and a $C_2H_4$ yield of 69.4%. After Reactor Two, the EtOH conversion rises to 95.0% for a $C_2H_4$ selectivity of 98.0% and a $C_2H_4$ yield of 93.1%.

A comparison of the data for Ex 4 and 5 with data for CEx E and F shows that with the same inlet temperature to the first reactor the layered or stacked catalyst bed of Ex 5 and 6 with no heating between the catalyst beds or reactors provides a higher EtOH conversion, higher $C_2H_4$ selectivity and higher $C_2H_4$ yield relative to use of a conventional single dehydration catalyst system in each of Reactors One and Two with heating between the Reactors as portrayed by CEx E and F in which the effluent from the first reactor is heated to the same temperature as the first reactor inlet temperature so that the two inlet temperatures are the same.

For Ex 6, replicate Ex 4 (Reactor One inlet temperature of 375° C.) but change the catalyst bed in Reactor Two to be the same as that of the catalyst bed in Reactor One and also heat the effluent from Reactor One to provide a Reactor inlet temperature of 375° C. Effluent from Reactor One shows an EtOH conversion of 84.6% for a $C_2H_4$ selectivity of 87.4% and a $C_2H_4$ yield of 73.9%. After Reactor Two, the EtOH conversion rises to 96.2% for a $C_2H_4$ selectivity of 97.2% and a $C_2H_4$ yield of 93.5%.

For Ex 7, replicate Ex 6 but change the Reactor One and Two inlet temperatures to 400° C. Effluent from Reactor One shows an EtOH conversion of 90.1% for a $C_2H_4$ selectivity of 93.2% and a $C_2H_4$ yield of 84.0%. After Reactor Two, the EtOH conversion rises to 98.9% for a $C_2H_4$ selectivity of 98.0% and a $C_2H_4$ yield of 97.0%.

For Ex 8, replicate Ex 7 but change the Reactor One and Two inlet temperatures to 425° C. Effluent from Reactor One shows an EtOH conversion of 98.9% for a $C_2H_4$ selectivity of 98.3% and a $C_2H_4$ yield of 97.2%. After Reactor Two, the EtOH conversion rises to 99.2% for a $C_2H_4$ selectivity of 98.0% and a $C_2H_4$ yield of 97.2%.

A comparison of the data for Ex 6-8 with that of CEx D-F shows the effectiveness of using two stacked catalyst beds with reheating of the effluent from Reactor One before it enters Reactor Two. The double stacked bed configuration of Ex 7 and Ex 8 in combination with inlet temperatures of, respectively 400° C. and 425° C. leads to essentially complete conversion of EtOH with correspondingly high selectivity to $C_2H_4$ (98.0%) and respective high $C_2H_4$ yields of 97.0% and 97.2%.

What is claimed is:

1. An adiabatic process for catalytically converting an alcohol contained in an alcohol feedstream to its corresponding olefin, which process comprises feeding the alcohol feedstream to a first dehydration catalyst bed in a series of two or more sequential dehydration catalyst beds under a first set of dehydration conditions to yield a partially dehydrated alcohol feedstream with a first olefin content and then feeding the partially dehydrated alcohol feedstream to a second sequential dehydration catalyst bed under a second set of dehydration conditions to yield a dehydrated alcohol feedstream with a second olefin content, the second olefin content being greater than the first olefin content, the first and second catalyst beds in each pairing of first and second catalyst beds comprising different catalysts and the first and second sets of dehydration conditions differing from one another by at least temperature with the first set of dehydration conditions comprising a temperature higher than the temperature of the second set of dehydration conditions.

2. The adiabatic process of claim 1, wherein the first dehydration catalyst bed contains gamma alumina.

3. The adiabatic process of claim 1, wherein the second dehydration catalyst bed contains a crystalline aluminosilicate zeolite catalyst.

4. The adiabatic process of claim 3, wherein the crystalline aluminosilicate zeolite catalyst is ZSM-5.

5. The adiabatic process of claim 1, wherein the first set of dehydration conditions includes a temperature within a range of from 325 degrees centigrade to 425 degrees centigrade.

6. The adiabatic process of claim 1, wherein the second set of dehydration conditions includes a temperature within a range of from 250 degrees centigrade to less than 375 degrees centigrade.

7. The adiabatic process of claim 1, wherein the series of two or more sequential dehydration catalyst beds comprises at least a third sequential dehydration catalyst bed with the dehydrated alcohol feedstream that has the second olefin content being a feedstream for the third sequential dehydration catalyst bed which operates under a set of dehydration conditions selected from a group consisting of the first set of dehydration conditions, the second set of dehydration conditions or a third set of dehydration conditions that differs from the first and second sets of dehydration conditions by at least temperature with the temperature of the third set of dehydration conditions being lower than that of the second set of dehydration conditions, with passage through the third sequential dehydration catalyst bed yielding a further dehydrated alcohol feedstream that has a third olefin content that is greater than the second olefin content.

8. The adiabatic process of claim 7, wherein the set of dehydration conditions for the third sequential bed is selected from the first set of dehydration conditions and the second set of dehydration conditions and the process further comprises heating the dehydrated alcohol feedstream to a temperature at which the selected set of dehydration conditions operates before the dehydrated alcohol feedstream contacts the third sequential bed.

9. The adiabatic process of claim 1, wherein the process comprises at least a first series of two or more sequential dehydration catalyst beds and a second series of at least the first sequential dehydration catalyst bed and the second sequential dehydration catalyst bed, with the dehydrated alcohol feedstream from the first series of two or more sequential dehydration catalyst beds comprising a feedstream for the first sequential dehydration catalyst bed of the second series of at least the first sequential dehydration catalyst bed and the second sequential dehydration catalyst bed, both of which operate under their respective operating conditions, the dehydrated alcohol feedstream being heated to a temperature at which the first sequential dehydration catalyst bed in the second series of at least the first sequential dehydration catalyst bed and the second sequential dehydration catalyst bed operates, whereby the first sequential dehydration catalyst bed and its associated operating conditions converts the dehydrated alcohol feedstream with its second olefin content to a further dehydrated alcohol feedstream with a third olefin content that is greater than the second olefin content and the second sequential dehydration catalyst bed and its associated operating conditions converts the further dehydrated alcohol feedstream to a still further dehydrated alcohol feedstream with a fourth olefin content that is greater than the third olefin content.

* * * * *